US009858394B2

United States Patent
Sudharsan

(10) Patent No.: US 9,858,394 B2
(45) Date of Patent: Jan. 2, 2018

(54) SYSTEMS AND METHODS FOR MANAGING REGIMEN ADHERENCE

(71) Applicant: WellDoc, Inc., Columbia, MD (US)

(72) Inventor: Bharath Sudharsan, Baltimore, MD (US)

(73) Assignee: WellDoc, Inc., Columbia, MD (US)

(*) Notice: Subject to any disclaimer, the term of this patent is extended or adjusted under 35 U.S.C. 154(b) by 32 days.

(21) Appl. No.: 15/360,209

(22) Filed: Nov. 23, 2016

(65) Prior Publication Data

US 2017/0076064 A1    Mar. 16, 2017

Related U.S. Application Data

(63) Continuation of application No. 14/312,229, filed on Jun. 23, 2014.

(60) Provisional application No. 61/839,528, filed on Jun. 26, 2013.

(51) Int. Cl.
| | |
|---|---|
| G06Q 50/22 | (2012.01) |
| G06Q 50/24 | (2012.01) |
| G06F 19/00 | (2011.01) |
| G06N 5/04 | (2006.01) |

(52) U.S. Cl.
CPC ........ *G06F 19/3456* (2013.01); *G06F 19/328* (2013.01); *G06F 19/345* (2013.01); *G06F 19/3437* (2013.01); *G06F 19/3443* (2013.01); *G06N 5/04* (2013.01); *G06N 5/048* (2013.01)

(58) Field of Classification Search
CPC ............................. G06Q 10/00; G06Q 50/00
USPC ...................................................... 705/2, 3
See application file for complete search history.

(56) References Cited

U.S. PATENT DOCUMENTS

| | | |
|---|---|---|
| 8,838,513 B2 | 9/2014 | Sudharsan |
| 9,064,040 B2 | 6/2015 | Sudharsan |
| 2003/0208113 A1 | 11/2003 | Mault et al. |
| 2008/0201174 A1* | 8/2008 | Ramasubramanian ............... G06F 19/3456 705/3 |
| 2012/0246102 A1 | 9/2012 | Sudharsan |

(Continued)

OTHER PUBLICATIONS

Improving quality of life of elderly people aged 85 and older by improving treatment adherence, Ioana Dana Alexa; Gabriel Ioan Prada; Valer Ioan Donca; Liana Mioara Mos; Ovidiu Alexa E-Health and Bioengineering Conference (EHB), 2013 Year: 2013 pp. 1-4, DOI: 10.1109/EHB.2013.6707380, IEEE Conference Publications.

(Continued)

*Primary Examiner* — Sean K Hunter
*Assistant Examiner* — Charles P Coleman
(74) *Attorney, Agent, or Firm* — Bookoff McAndrews, PLLC

(57) ABSTRACT

Systems and methods are provided for managing medical adherence. An exemplary method may include managing medical adherence utilizing data aggregating and processing to determine impact on a user's health based on their behavior related to prescribed medication. The method may entail utilizing data related to a medication regimen and patient behavior to determine a patient's compliance to the regimen in terms of dosage and time. These values may be utilized to calculate a medical adherence value representing a patient's adherence to a prescribed regimen. Responsive to determining low medical adherence, a notification may be generated which may result in an intervention with the patient.

20 Claims, 7 Drawing Sheets

(56) References Cited

U.S. PATENT DOCUMENTS

| | | | |
|---|---|---|---|
| 2013/0226608 A1* | 8/2013 | Di Lascia | G06F 19/3431 |
| | | | 705/2 |
| 2014/0155705 A1* | 6/2014 | Papadopoulos | G06F 19/3481 |
| | | | 600/301 |
| 2014/0207486 A1* | 7/2014 | Carty | G06Q 50/22 |
| | | | 705/2 |
| 2014/0249851 A1* | 9/2014 | Christodouleas | G06F 19/325 |
| | | | 705/3 |
| 2014/0358581 A1 | 12/2014 | Sudharsan | |
| 2015/0006192 A1 | 1/2015 | Sudharsan | |
| 2015/0006456 A1 | 1/2015 | Sudharsan | |
| 2015/0006462 A1 | 1/2015 | Sudharsan | |
| 2015/0248533 A1 | 9/2015 | Sudharsan | |

OTHER PUBLICATIONS

Medication adherence system using SMS technology, I. Sachpazidis; S. Fragou; G. Sakas Intelligent Sensors, Sensor Networks and Information Processing Conference, 2004. Proceedings of the 2004, Year: 2004, pp. 571-575, DOI: 10.1109/ISSNIP.2004.1417524, IEEE Conference Publications.

An intelligent medication system designed to improve the medication adherence, Marias A. S. Rodrigues; Vandermi J. Silva; Vicente F. de Lucena Consumer Electronics—Berlin (ICCE-Berlin), 2015 IEEE 5th International Conference on Year: 2015, pp. 46-49, DOI: 10.1109/ICCE-Berlin.2015.7391310, IEEE Conference Publications.

Medication adherence using a smart pill bottle, Dana DeMeo; Michael Morena Emerging Technologies for a Smarter World (CEWIT), 2014 11th International Conference & Expo on Year: 2014, pp. 1-4, DOI: 10.1109/CEWIT.2014.7021149, IEEE Conference Publications.

\* cited by examiner

SYSTEMS AND METHODS FOR MANAGING REGIMEN ADHERENCE

CROSS-REFERENCE TO RELATED APPLICATIONS

This application is a continuation of U.S. patent application Ser. No. 14/312,229, filed Jun. 23, 2014, which claims the benefit of priority to U.S. Provisional Application No. 61/839,528, entitled "Systems and Methods for Managing Patient Conditions," filed Jun. 26, 2013, the entireties of each of which are incorporated herein by reference.

TECHNICAL FIELD

Various embodiments of the present disclosure relate generally to managing medical adherence. More specifically, particular embodiments of the present disclosure relate to systems and methods for managing medical adherence utilizing data aggregation and processing the data to determine impact on a patient's health based on their behavior related to a prescribed medication.

BACKGROUND

An important aspect of medical care is medication management. In fact, medication adherence, that is, a patient's utilization of the prescribed regimen of medication on time and in the correct dosage, is directly related to the success of the treatment or management of a medical condition. For example, organ transplant patients may be prescribed pills in the order of 30-50 per day that have to be consumed at specific times through the day. Inconsistency in adherence to the prescribed regimen may have serious short-term and long-term consequences, such as organ rejection or even death. Mismanagement of regimens associated with other medical conditions, such as HIV, allergies, diabetes, asthma, hypertension, may also lead to similar consequences that range from causing discomfort to being lethal.

Typically, various health service provides, provide "pillbox" type resources to monitor medication adherence. These resources are limited to providing users with reminders of the medicine they have taken or simply keeping a record of actions related to compliance with a medication regimen.

However, it can be difficult for a healthcare provider to efficiently manage a patient's medical adherence utilizing such an approach to improve a patient's health or clinical outcomes.

SUMMARY OF THE DISCLOSURE

Embodiments disclose systems and methods for managing a patient's medical adherence, specifically adherence to medication.

According to some embodiments, computer-implemented methods are disclosed for managing a patient's medical adherence. In an exemplary method, the method includes receiving data related to the patient, the data including information related to a medication regimen associated with the patient that includes one or more medications, patient behavior data, a respective literacy level associated with each of the one or more medications. The method further includes calculating a compliance to dosage and a compliance to time for each of the one or more medications based on the received data and, thereafter, calculating a drug adherence count associated with each of the one or more medications by summing at least two of the compliance to dosage, the compliance to time, and the respective literacy level associated with each of the one or more medications. The method may also include determining a daily medication adherence for each of the one or more medications, calculating a daily regimen adherence value by summing the daily medication adherence of all of the one or more medications in the medication regimen, calculating a daily regimen baseline value by re-calculating the daily regimen adherence value by utilizing a maximum potential value for the drug adherence count for each of the respective medications in the regimen associated with the patient. The method may further include, determining a medical adherence value based on the daily regimen adherence value and the daily regimen baseline value, and comparing the medical adherence with a threshold value.

According to some embodiments, systems are disclosed for managing a patient's medical adherence. One system includes a memory having processor-readable instructions stored therein and a processor configured to access the memory and execute the processor-readable instructions, which when executed by the processor configures the processor to perform a method. In an exemplary method, the method includes receiving data related to the patient, the data including information related to a medication regimen associated with the patient that includes one or more medications, patient behavior data, a respective literacy level associated with each of the one or more medications. The method further includes calculating a compliance to dosage and a compliance to time for each of the one or more medications based on the received data and, thereafter, calculating a drug adherence count associated with each of the one or more medications by summing at least two of the compliance to dosage, the compliance to time, and the respective literacy level associated with each of the one or more medications. The method may also include determining a daily medication adherence for each of the one or more medications, calculating a daily regimen adherence value by summing the daily medication adherence of all of the one or more medications in the medication regimen, calculating a daily regimen baseline value by re-calculating the daily regimen adherence value by utilizing a maximum potential value for the drug adherence count for each of the respective medications in the regimen associated with the patient. The method may further include, determining a medical adherence value based on the daily regimen adherence value and the daily regimen baseline value, and comparing the medical adherence with a threshold value.

According to some embodiments, a non-transitory computer readable medium is disclosed as storing instructions that, when executed by a computer, cause the computer to perform a method, the method includes receiving data related to the patient, the data including information related to a medication regimen associated with the patient that includes one or more medications, patient behavior data, a respective literacy level associated with each of the one or more medications. The method further includes calculating a compliance to dosage and a compliance to time for each of the one or more medications based on the received data and, thereafter, calculating a drug adherence count associated with each of the one or more medications by summing at least two of the compliance to dosage, the compliance to time, and the respective literacy level associated with each of the one or more medications. The method may also include determining a daily medication adherence for each of the one or more medications, calculating a daily regimen adherence value by summing the daily medication adherence of all of the one or more medications in the medication regimen, calculating a daily regimen baseline value by re-calculating the daily regimen adherence value by utilizing a maximum potential value for the drug adherence count for each of the respective medications in the regimen associated with the patient. The method may further include, determining a medical adherence value based on the daily regimen adherence value and the daily regimen baseline value, and comparing the medical adherence with a threshold value.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

While the present disclosure is described herein with reference to illustrative embodiments for particular applications, it should be understood that embodiments of the present disclosure are not limited thereto. Other embodiments are possible, and modifications can be made to the described embodiments within the spirit and scope of the teachings herein, as they may be applied to the above-noted field of the present disclosure or to any additional fields in which such embodiments would be of significant utility.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In view of the challenges associated with the conventional techniques outlined above, systems and methods are disclosed herein for managing medication adherence.

Reference will now be made in detail to the exemplary embodiments of the disclosure, examples of which are illustrated in the accompanying drawings. Wherever possible, the same reference numbers will be used throughout the drawings to refer to the same or like parts.

Figure 1:
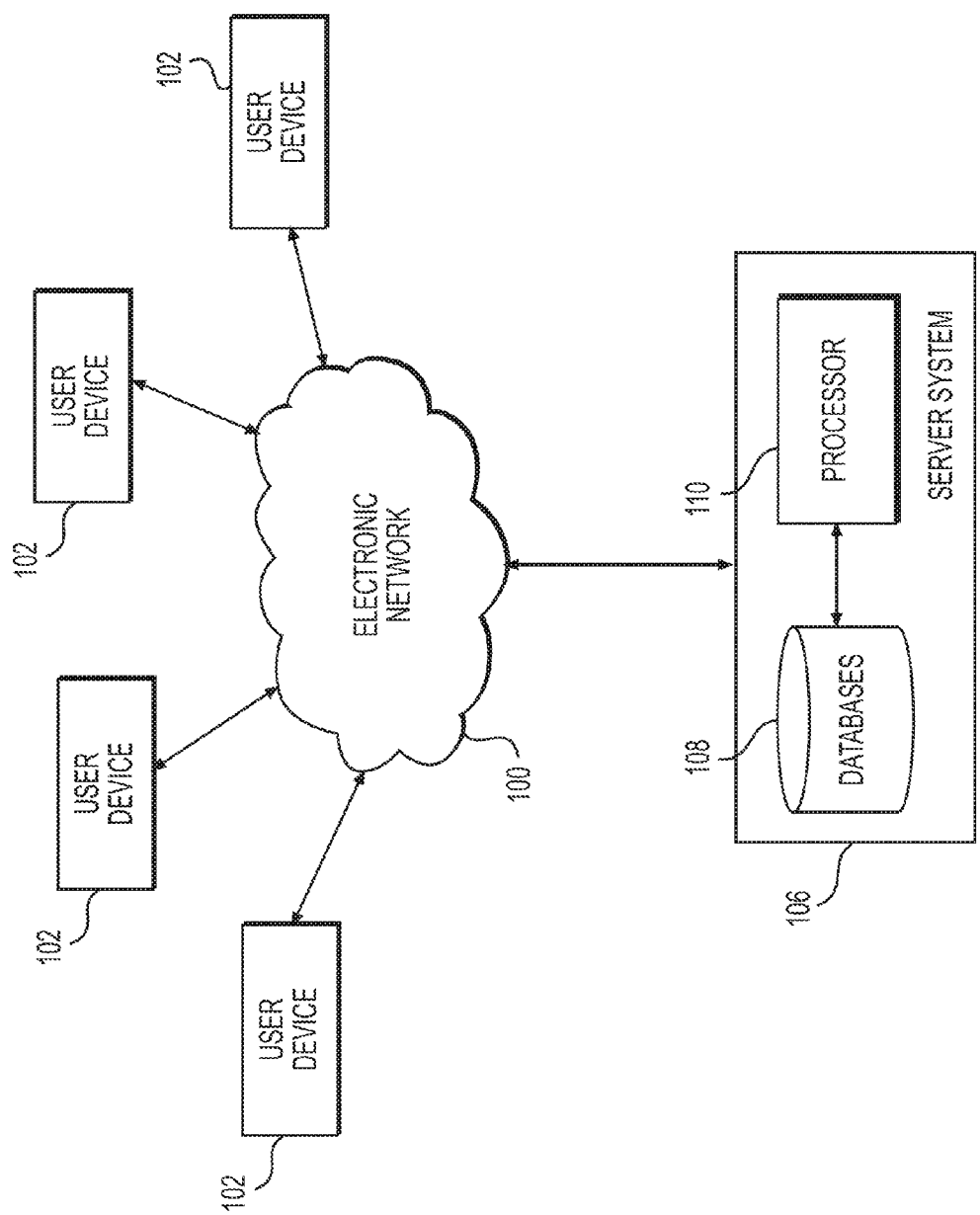
FIG. 1 is a schematic diagram of a network environment for managing medical adherence, according to an embodiment of the present disclosure.

FIG. 1 is a schematic diagram of an exemplary network environment in which various systems may manage and monitor medical adherence, according to an embodiment of the present disclosure. As shown in FIG. 1, the environment may include a plurality of user or client devices 102 that are communicatively coupled to each other as well as one or more server systems 106 via an electronic network 100. Electronic network 100 may include one or a combination of wired and/or wireless electronic networks. Network 100 may also include a local area network, a medium area network, or a wide area network, such as the Internet.

In one embodiment, each of user or client devices 102 may be any type of computing device configured to send and receive different types of content and data to and from various computing devices via network 100. Examples of such a computing device include, but are not limited to, mobile health devices, a desktop computer or workstation, a laptop computer, a mobile handset, a personal digital assistant (PDA), a cellular telephone, a network appliance, a camera, a smart phone, an enhanced general packet radio service (EGPRS) mobile phone, a media player, a navigation device, a game console, a set-top box, a biometric sensing device with communication capabilities, or any combination of these or other types of computing devices having at least one processor, a local memory, a display (e.g., a monitor or touchscreen display), one or more user input devices, and a network communication interface. The user input device(s) may include any type or combination of input/output devices, such as a keyboard, touchpad, mouse, touchscreen, camera, and/or microphone.

In one embodiment, each of the user or client devices 102 may be configured to execute a web browser, mobile browser, or additional software applications that allows for input from patients and other individuals from the medical field including physicians, nurses, pharmacists, etc. One or more of user or client devices 102 may be further configured to execute software allowing for monitoring of patient behavior including the ability to receive user input or utilizing associated sensors to monitor patient behavior. For example, user or client devices 102 may contain an application which allows it to receive data from a paired and/or integrated blood sugar level monitor and then transmit the data to other entities within environment 100. Alternatively, user or client devices 102 may contain applications which allow for a patient to input information related to patient behavior such as consumption of medication, including, but not limited to, dosage and/or compliance information.

Server system 106 in turn may be configured to receive data related to a medication regimen, individual medications in a medication regimen, patient, patient behavior, etc. It should be noted that while a singular server system 106 is described, method 200, described below with respect to FIG. 2, may be implemented using a plurality of server systems working in combination, a single server device, or a single system.

Also, as shown in FIG. 1, server system 106 may include one or more databases 108. In an embodiment, databases 108 may be any type of data store or recording medium that may be used to store any type of data. For example, databases 108 may store data received by or processed by server system 106 including information related to a patient's prescribed regimen, including timings and dosages associated with each medication of the regimen. Databases 108 also may store information related to the patient including their literacy level related to each of the prescribed medications.

Additionally, as shown in the example of FIG. 1, server system 106 may include processor 110. In an embodiment, processor 110 may be configured to execute a process for managing medical adherence. The management process may, for example, continue to constantly monitor regular (e.g., daily, weekly, monthly, etc.) compliance to time and dosage of a medical regimen. Utilizing these values along with additional factors, metrics may be generated which efficiently indicate a patient's overall adherence to a medication regimen.

In an embodiment, processor 110 may be configured to receive instructions and data from various sources including user or client devices 102 and store the received data within databases 108. In some implementations, any received data may be stored in the databases 108 in an encrypted form to increase security of the data against unauthorized access and complying with HIPAA privacy regulations. Processor 110 or any additional processors within server system 106 also may be configured to provide content to client or user devices 102 for display. For example, processor 110 may transmit displayable content including messages or graphic user interfaces soliciting information related to patient behavior.

Figure 2:
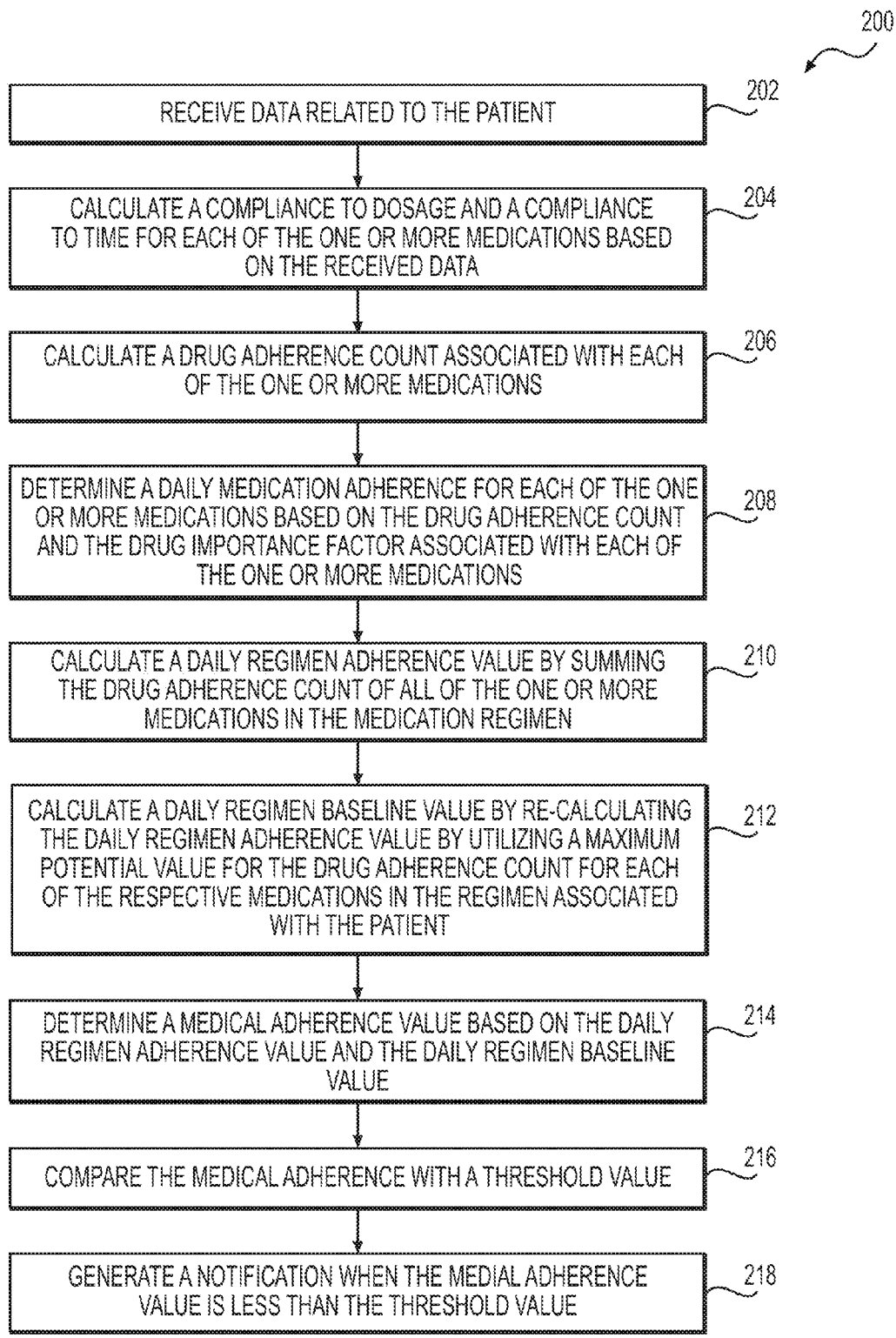
FIG. 2 is a flow diagram of an exemplary method for managing medical adherence, according to an embodiment of the present disclosure.

FIG. 2 is a flow diagram of a method 200 for managing a patient's medical adherence, according to an embodiment of the present disclosure.

In step 202, method 200 includes receiving data related to the patient. For example, this data may be received and/or retrieved by processor 110 from one or more databases 108 or may be directly received from one or more user or client devices 102. The data may include information related to a medication regimen associated with the patient that includes one or more medications, patient behavior data (e.g. objective and subjective data), a respective literacy level associated with each of the one or more medications, and a respective drug importance factor associated with each of the one or more medications. This received data may previously be generated utilizing processor 110 and stored in databases 108. Alternatively, the received data may be transmitted by one of user or client devices 102, including data previously transmitted and stored in databases 108. In embodiments, one of user or client devise 102 may transmit data in real time, continuously, periodically, or based on a predetermined duty cycle.

In embodiments, information related to a medication regimen, may include information regarding all the medicine included in the regimen including prescribed dosage and times related to the medication.

In additional embodiments, this information may include unique identities assigned to the regimen and unique identities assigned to each of the one or more medications in the regimen allowing for easier management of data. For example, in the case of multiple diseases for which a patient may be treated, regimen identities may be assigned by multiples of 100. For example, a first disease regimen number may be 100, a second disease regimen number may be 200, and henceforth. As discussed earlier, each regimen may contain one or more medications prescribed by a physician. Each medication in a regimen may be assigned a unique number for identification. For example, $D_{[i,j]}$, $D_{[i,j+1]}$ ... $D_{[i,n\#i]}$, where Medication ID=subscript 1, subscript 2. Here, Here subscript 1 (e.g., i) refers to the regimen number and subscript 2 (e.g., j, j+1, ...) refers to the ID of the medication in the same regimen. The regimen numbers may be assigned in incremental manner sequentially starting from first regimen of the patient.

Accordingly, while data related to a medical regimen may be captured based on the original medication name, the data may be managed in an easier manner by assigning each medication a unique identity utilizing the naming convention discussed above. In some embodiments, other suitable name/identifying conventions may be used with the principle of this disclosure.

Figure 3A:
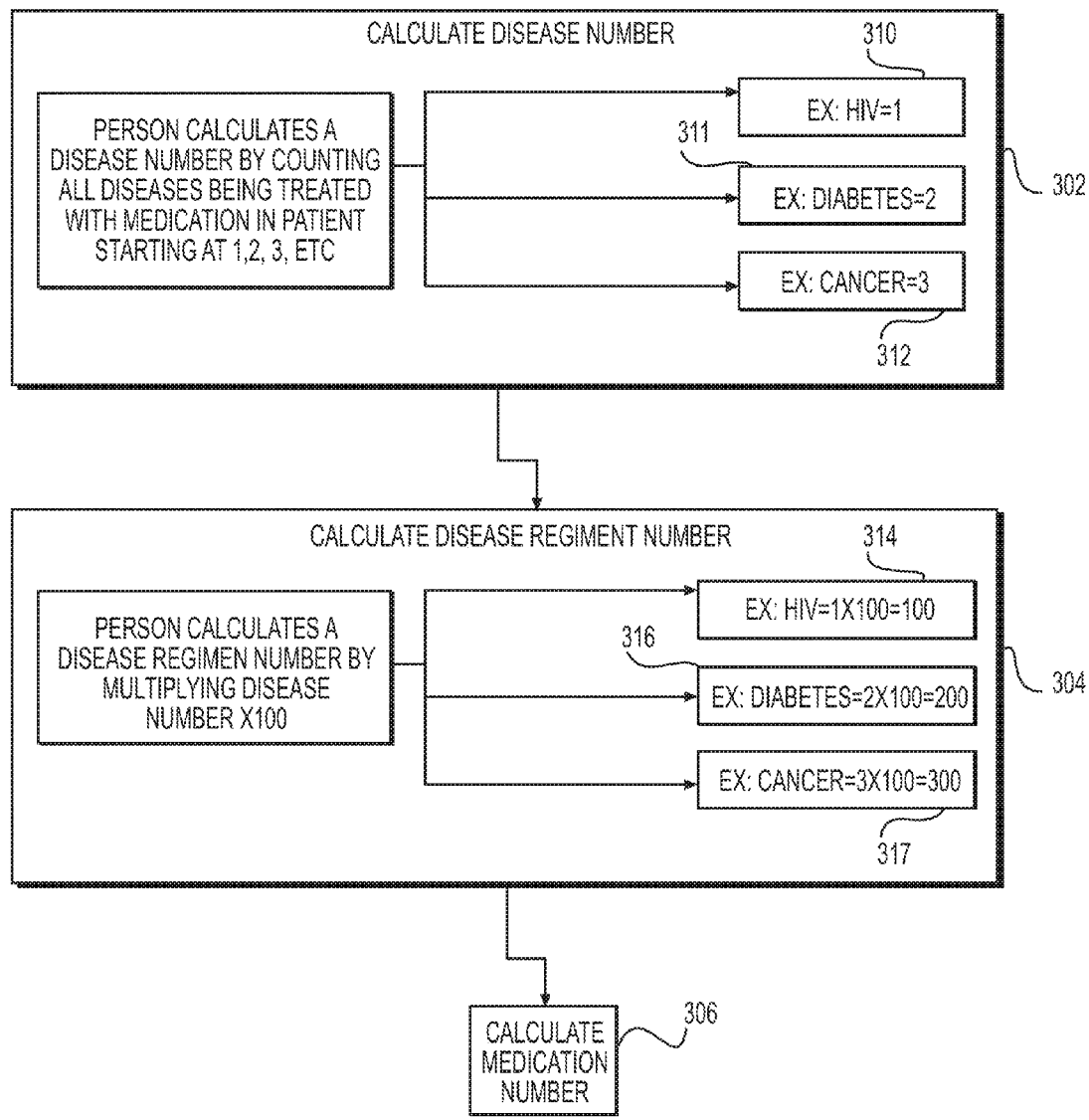
FIGS. 3A and 3B illustrate an exemplary implementation of calculating the regimen number and assigning unique identification numbers, according to an embodiment of the present disclosure.
Figure 3B:
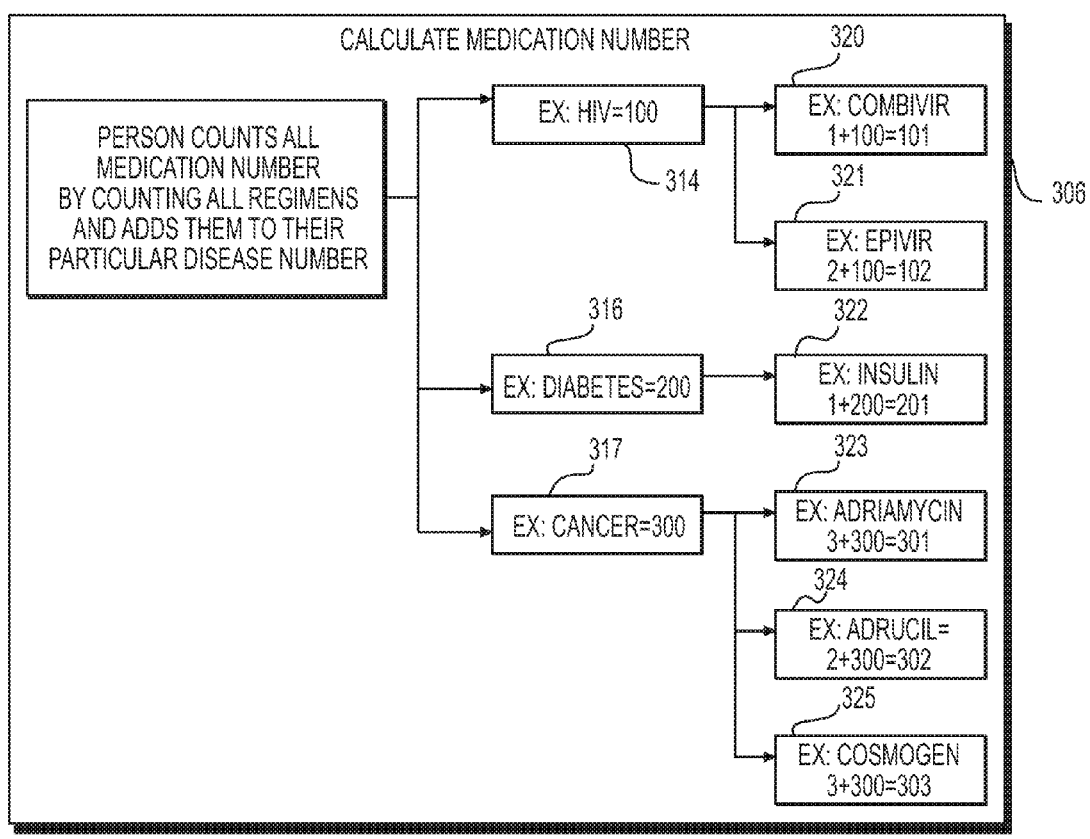
Figure 4:
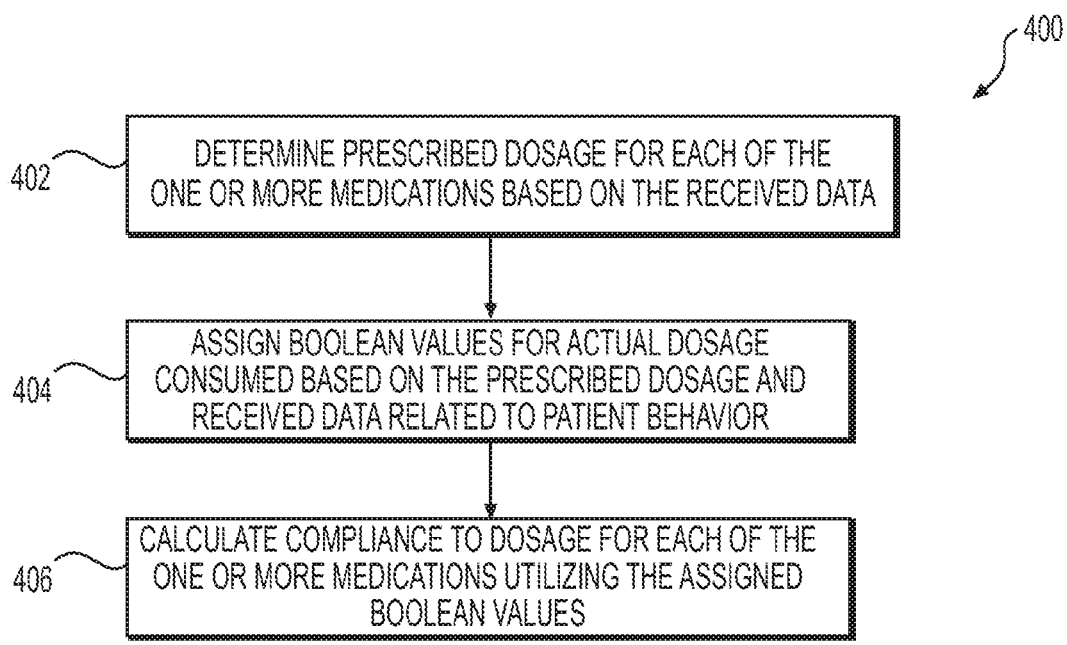
FIG. 4 is a flow diagram of an exemplary method for calculating compliance with dosage, according to an embodiment of the present disclosure.
Figure 5:
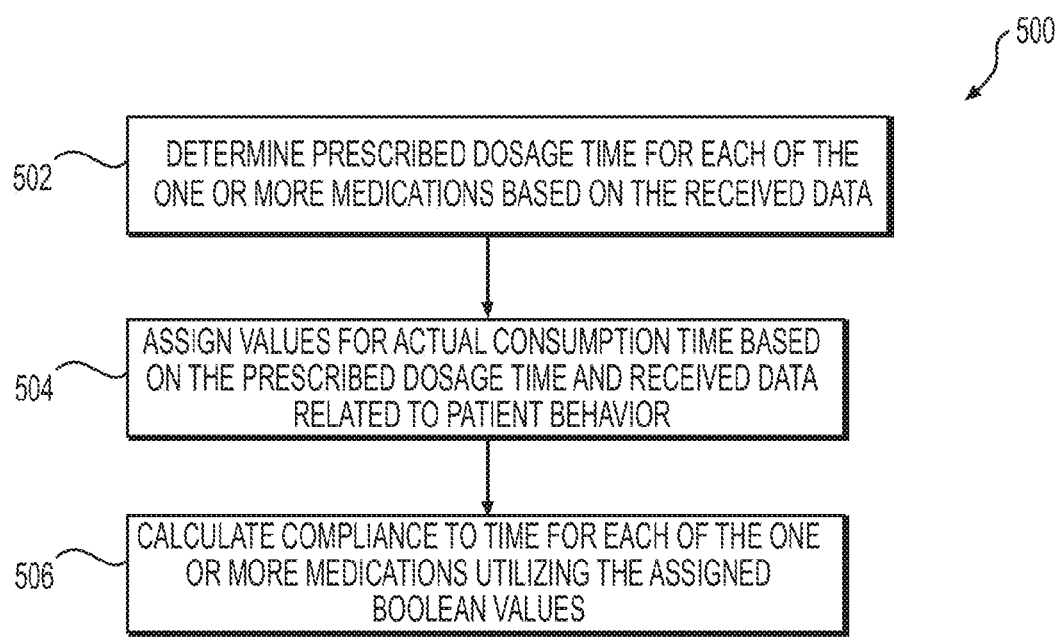
FIG. 5 is a flow diagram of an exemplary method for calculating compliance with time, according to an embodiment of the present disclosure.

For example, FIGS. 3A and 3B illustrate an exemplary implementation of calculating the regimen number and assigning unique identification numbers, according to an embodiment of the present disclosure. Step 308 entails assigning each respective disease a unique disease number, disease 310 (HIV) is assigned a "1," disease 311 (diabetes) is assigned a "2," and disease 312 (cancer) is assigned a "3." Thereafter, in step 304, each of the assigned numerical values are multiplied by 100 to produce disease regimen numbers 314, 316, and 317 for the respective diseases. The disease numbers from step 304 are then utilized to calculate medication number in step 306. Step 306 is illustrated in more detail in FIG. 3B. Using the disease regimen numbers 314, 316, and 317, the mediation numbers are calculated by incrementally adding an incremental integer value to the disease number starting with 1 for each respective medication associated with the regimen. For example, for disease 310 (HIV), for a first medication 320 (Comibir) associated with disease regimen number 314, a 1 is added to 100 to calculate a medication number value of 101. For a second medication 321 associated with disease regimen number 314, a 2 is added to 100 to calculate a medication number value of 101. The medication numbers for medications 322, 323, 324, and 325 are similarly calculated based on the associations of these medications with respective disease regimens 316 and 317. In some embodiments, these values then may be stored in databases 108.

In embodiments, patient behavior data may refer to data related to patient behavior including when and if a patient complied with recommendations of a regimen For example, patient behavior data may indicate that a patient orally consumed a certain dosage of medication at various specific times such as 8 a.m., 2 p.m., and 8 p.m. daily.

In embodiments, literacy level (LL) is a metric to assess the familiarity of a patient with a prescribed regimen and its medications. This value may be calculated or updated based on various conditions. In a first exemplary condition, a patient may be asked to take a survey with questions related to literacy regarding medical adherence for the unique regimen. This survey or observations by a physician regarding a patient's knowledge base may be utilized to set the baseline literacy level for a patient's particular regimen. The score based on a survey or a physician's observations may be updated subsequently based on additional surveys or observations. In a second exemplary condition, the literacy level may be impacted by determination that erroneous medication data was entered by a patient using user or client device 102 a threshold amount of times over a particular period. For example, in monitoring daily medication adherence over a week, it may be determined that the patient entered erroneous medication data or did not enter any medication data a threshold amount of times in the week. Thereafter, the assigned literacy level to the regimen may be dropped. In a third exemplary condition, the literacy level may be impacted based on occurrence of a condition based on lack of medical adherence by a patient. For example, if there are any ill effects based on user behavior, such as lowering of blood sugar levels due to missing medication.

In embodiments, intervention techniques, such as changing the types of medicine or motivational interviews with patients, may be applied in response to determination of low literacy levels. Motivational interviews may include a physician (or other medical professional) speaking with a patient, discussing benefits of following the regimen, and explaining impact of failure to do so. Thereafter, levels of error, ill effects, and survey results may be reassessed after a certain time period, such as daily, weekly, monthly basis.

In embodiments, drug importance factor (DIF) may be entered by a medical professional (e.g., physician, pharmacist, physician's assistant, etc.) associated with a patient's medical regimen utilizing a user or client device 102. This value may allow for defining a relative importance of a given medication with respect to other medications in the same regimen for a specific patient or disease being treated. In detail, data related to the assignment of drug importance factors may be assigned by a physician during medication validation. While a physician may utilize a comparison or relativity in their thought process for assigning the drug importance factor, each medication in a regimen is assigned a drug importance factor without any contingency on any other medication. As an example, a physician may be provided with a data entry field next to each medication to weigh its importance for the prescribed regimen, on a scale of 1 to 3. In such an example, it is possible for all medications in a regimen to get an assigned value of 3 each if found important. Alternatively, any suitable scale may be used which is consistence with the principle of the present disclosure. However, in embodiments, a minimum of 1 is assigned in order to ensure all medications obtain a non-zero value for the purposes of being able to calculate a daily medication adherence as is discussed in further details below.

In an additional embodiment, for calculating the drug importance factor (DIF), the rationale behind a physician's drug importance factor scoring may be partially supplemented by using pharmacokinetic techniques. The drug importance factor baseline may be based on clinical data or set by a certified pharmacologist by examining interrelationships between medications and hence their effects on similar patients.

In step 204, method 200 includes calculating a compliance to dosage and a compliance to time for each of the one or more medications based on the received data.

Regarding compliance to dosage, this value may be calculated utilizing exemplary method 400. In step 402, step 400 includes determining prescribed dosage for each of the one or more medications based on the received data. That is, the presence disclosure contemplates utilizing information regarding the prescribed regimen to determine dosage associated with each of the one or more medications. For example, this may be based on the prescription information input by a physician or a physician's assistant in-charge of providing medical services to a patient.

In step 404, method 400 includes assigning boolean (or binary) values for actual dosage consumed based on the prescribed dosage and received data related to patient behavior. For example, data associated with patient behavior may indicate whether a patient consumed a particular prescribed dosage. Accordingly, in an exemplary embodiment, when a dosage is consumed, a value of "1" may be assigned, while when a dosage is not consumed a value of "0" might be assigned. Since, a patient may consume an inaccurate amount of the prescribed dosage, different thresholds may be assigned regarding whether a partial consumption leads to an assignment of "1" or "0" value. For example, if a dosage of three pills of a first medication is assigned and the patient consumes only two out of the three pills, a boolean may be assigned a "1" if a threshold value is preset so that anything higher than a 60% consumption of a dosage is considered to be compliant. This threshold amount may be preset by a medical professional taking into account in the importance of the medicine, impact on variations in dosage, and other additional factors.

In step 406, method 400 includes calculating compliance to dosage for each of the one or more medications utilizing the assigned boolean values. For example, for ten dosages prescribed throughout the day, the boolean values may be utilized to calculate an overall value for the day. For example, if 8 out of 10 prescribed dosages for a particular medication where complied with throughout the day, then the actual consumed dosage would be assigned a "1" for those 8 instances and a "0" would be assigned for the other two instances. Accordingly, a compliance value of 0.8 may be calculated for the compliance to dosage for that particular medicine by dividing the overall boolean value with the total prescribed instances.

In additional embodiments, the compliance to dosage may simply be a ratio of dosage consumed to total dosage prescribed. For example, if a patient was prescribed 10 units of a medication in a day and took only 8 units, then the respective compliance to disease is obtained by dividing the amount of units actually consumed by the prescribed units. In this instance, it would be 8/10 which equals 0.8.

Compliance to dosage may provide valuable information about a patient's behavior. For example, an indication regarding a trend in a rise or drop of medication taken may be very significant for certain patients, such as patients on a short acting insulin regimen to control their diabetes.

Regarding compliance to time, this interaction may be calculated utilizing exemplary method 500. In step 502, method 500 includes determining prescribed dosage time for each of the one or more medications based on the received data. That is, utilize information regarding the prescribed regimen to determine the time when each of the one or more medications is to be consumed. For example, this may be the prescription information input by a physician or a physician's assistant in-charge of providing medical services to a patient.

In step 504, method 500 includes assigning boolean (or binary) values for actual consumption time based on the prescribed dosage time and received data related to patient behavior. For example, data associated with patient behavior may indicate the time a patient consumed a particular dosage. Accordingly, in an exemplary embodiment, when a dosage is consumed at the correct time, a value of "1" may be assigned, while when a dosage is not consumed at a prescribed time, a value of "0" might be assigned. Since, a patient may not always consume the medicine at the prescribed time, a threshold amount of time may be set which is considered as still complying with the regimen. For example, if a threshold of 15 minutes is set, then if the patient consumes a dosage fifteen minutes before or after a prescribed time of 6 p.m., the consumed dosage may be considered to be complying with the prescribed dosage time.

The threshold amount of time may be preset by a medical professional taking into account in the importance of the medicine, impact on variations in dosage, and other additional factors including, but not limited to availability of the prescribed medication.

In step 506, method 500 includes calculating compliance to time for each of the one or more medications utilizing the assigned boolean values. For example, for ten dosages prescribed throughout the day, the boolean values may be utilized to calculate an overall value for the day. For example, if 8 out of 10 actual consumption times for a particular medication complied with the prescribed dosage times, then the actual consumption time would be assigned a "1" for those 8 instances and a "0" would be assigned for the other two instances. Accordingly, a compliance value of 0.8 may be calculated for the compliance to time for that particular medicine by dividing the overall boolean value with the total instances.

In additional embodiments, the compliance to time may simply be a function of the time delays associated with consumed dosages. For example, the prescribed times for dosages may be utilized as a baseline, and every instance of non-compliance of time related to a dosage may result in a drop in the compliance to time value. In embodiments, the drops in a compliance to time value may be proportional to the time delays and/or early consumption.

In some embodiment, the compliance to time may be a function of times and dosage. For example, consumption of a prescribed amount of medication at the suggested time would count as 100 percent compliance for that instance. However, a five minute delay may count as 75% compliance, a ten minute delay may count as 50% compliance, and so on and so forth, until a time when the prescribed dose is considered to have zero percent compliance. The times for the percent of compliance may be set based on pharmaceutical and clinical research associated with the effectiveness of a medication, and other factors. For example, if insulin is to be injected by a diabetes patient at 2 p.m. with an expectation of a meal to be consumed at 2:30 p.m., then injecting it at 2:30 p.m. may not have the desired impact that injecting it on schedule would have.

With reference to FIG. 2, in step 206, method 200 further includes calculating a drug adherence count (DAC) associated with each of the one or more medications. In detail, the drug adherence count may be calculated by summing at least two of the compliance to dosage (CD), the compliance to time (CT), and the respective literacy level (LL) associated with each of the one or more medications. In embodiments, the drug adherence count may be calculated by summing all three of the compliance to dosage (CD), the compliance to time (CT), and the respective literacy level (LL) associated with each of the one or more medications.

In embodiments, drug adherence count (DAC) serves as a metric that efficiently accounts for a consumed medication including compliance with respective prescribed time of the day when it is supposed to be taken, compliance with respective prescribed dosage of the medication, and a patient's literacy about the medications the regimen. In an exemplary embodiment, the calculation of DAC may be presented in an equation as follows:

$$DAC=CD+CT+LL$$

In step 208, method 200 includes determining a daily medication adherence (DDA) for each of the one or more medications based on the drug adherence count (DAC) and the drug importance factor (DIF) associated with each of the one or more medications. In embodiments, the daily medication adherence is determined by multiplying the drug adherence count by the drug importance factor associated with each of the one or more medications. In embodiments, daily medication adherence is a metric which aids in efficiently indicating adherence towards the proscribed regimen by adding relative weightage to medication that is considered more relevant or important. Continuing the example from step 206, the calculation for determining the DDA may be presented in an equation, as follows:

$$DDA=DAC \times DIF$$

In step 210, method 200 includes calculating a daily regimen adherence (DRA) value by summing the daily medication adherence of all of the one or more medications in the medication regimen. In embodiments, allowing for the summing of the daily medication adherence for each of the or the or more medications in a regimen, allows for a singular value which efficiently represents adherence for the whole regimen. This allows for an efficient and quick monitoring of a prescribed regimen, instead of straining resources, such as time, to look at compliance for each individual medication.

Continuing the example from step 208, the daily regimen adherence (DRA) is a sum of DDA for medications $D_{[i,j]}$, $D_{[i,j+1]} \ldots D_{[i,n\#i]}$.

In step 212, method 200 includes calculating a daily regimen baseline value (DRB) by re-calculating the daily regimen adherence value by utilizing a maximum potential value for the drug adherence count for each of the respective medications in the regimen associated with the patient. Accordingly, the daily regimen baseline value represents a value that would be achieved if there was ideal compliance to dosage and ideal compliance to time. This metric allows for contextualization of patient behavior in light of the prescribed medication regimen. An ideal patient should have equal values for both the daily regimen adherence value and the daily regimen baseline value.

As an example, a maximum value is assumed for DAC in DDA=DAC×DIF. Then the newly calculated DDAs are summed as in the case of calculating DRA for calculating the daily regimen baseline value (DRB).

In step 214, method 200 includes determining a medication adherence value (DA) based on the daily regimen adherence value and the daily regimen baseline value. For example, a ratio of the daily regimen adherence value and the daily regimen baseline value may serve as the medication adherence value. In instances, the determined ratio may be multiplied by a constant factor to ensure that the medication adherence value (DA) is an integer. For example, the following equation may be utilized:

$$DA=(DRA/DRB) \times 10$$

Accordingly, as an example if the DRA is 7 and the DRB is 10, the medical adherence value will be 7

In step 216, method 200 includes comparing the medication adherence with a threshold value. A threshold value may be set for a level where the clinical medical intervention may be necessary. For example, if a medical adherence value under 8 may have short-term or long-term consequences, than a threshold value of 8 may be set. This value may be set by a physician, based on clinical data, application of learning algorithms on clinical data (whether the patient's or broader set of patients), or a function of a combination of a physician's recommendations along with clinical data.

In additional embodiments, multiple threshold values may be set to which the medical adherence value is compared.

For example, a first threshold value may be a critical value which represents a serious lapse in adherence, which requires urgent intervention. A second threshold value may be an adherence value which is not critical but still of medical concern. For example, on a scale of 0-10, a value of 3 may be a critical value under which the adherence value must not drop. If it does, then the patient may require serious immediate care. On the other hand, a value of 8 may be significant enough to require investigation of possible intervention.

In step 218, method 200 includes generating a notification when the medial adherence value is less than the threshold value. In detail, once it is determined that the medication adherence value is less than the threshold value a notification may be generated that may be then provided to the patient or other concerned entities such as pharmacists, physicians, and clinicians, etc. The notifications may serve as reminders as well as instruments to force reconsideration of treatment plans and interventions.

In additional embodiments, medication adherence may be calculated for successive days. Thereafter, processor 110 may then calculate a variation of the medical adherence over successive days. A rise or drop over a threshold amount on successive days may also trigger a notification, since the rise or drop may indicate that a patient is not maintaining a stabilized dosage. The notification may prompt an intervention including prompting another literacy survey, in response to which a physician may personally intervene.

While the method 200 is explained with respect to a daily time period, the same principles may be applied to calculate a medical adherence for any user-selected time period including a week, a month, etc. The principle of the present disclosure may be used to monitor patient adherence to any medical regimen, including but not limited to, diagnostic testing, exercise, diet, etc.

In further embodiments, medical adherence values may be utilized in combination with other such self-management scores to obtain an overall health management score. Analytics framework may provide relationships between such scores for a patient, in order to identify violating parameters and correct them—all with the use of a single dashboard displaying these scores. Hence, exemplary embodiments aid in reducing the time for customers and physicians to make decisions about clinical issues, as well as enhancing accuracy of clinical decisions. Embodiments of the present disclosure are disease and population size agnostic, and therefore have applicability across the spectrum of healthcare matters.

In some embodiments, data related to a patient's medical adherence may be parsed and cleansed to comply with HIPPA privacy guidelines. Thereafter, the data may be provided to pharmaceutical companies or other entities to use behavioral data to modify their products and/or recommendations.

In additional embodiments, in addition to providing a physician information about a patient's medical adherence, modeling systems based on user behavior may be utilized to provide treatment recommendations to physicians. For example, providing suggesting to physician regarding medication that have a high level of medical adherence.

The examples described above with respect to FIGS. 1-5, or any part(s) or function(s) thereof, may be implemented using hardware, software modules, firmware, tangible computer readable media having instructions stored thereon, or a combination thereof and may be implemented in one or more computer systems or other processing systems.

Figure 6:
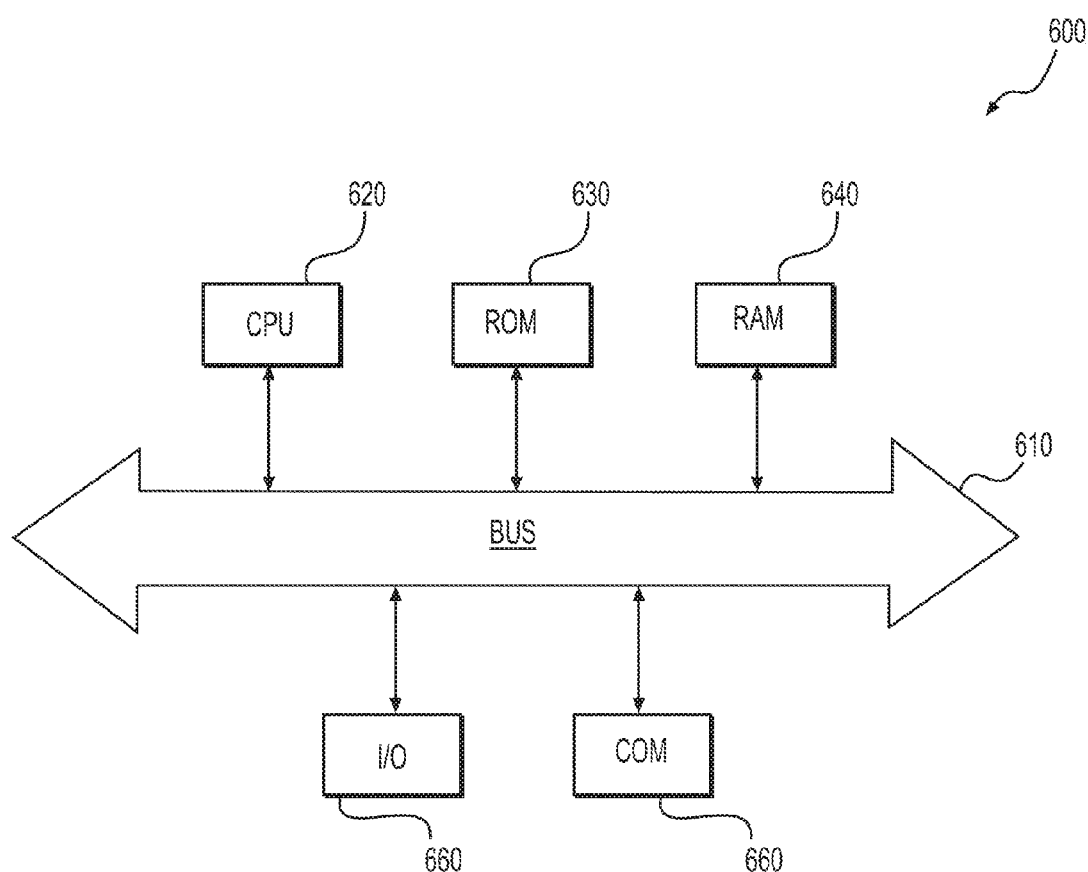
FIG. 6 is a block diagram of an exemplary computer system in which embodiments of the present disclosure may be implemented.

FIG. 6 illustrates a high-level functional block diagram of an exemplary computer system 600, in which embodiments of the present disclosure, or portions thereof, may be implemented, e.g., as computer-readable code. For example, each of the exemplary devices and systems described above with respect to FIG. 1 can be implemented in computer system 600 using hardware, software, firmware, tangible computer readable media having instructions stored thereon, or a combination thereof and may be implemented in one or more computer systems or other processing systems. Hardware, software, or any combination of such may embody any of the modules and components in FIG. 1, as described above.

If programmable logic is used, such logic may be executed on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, at least one processor device and a memory may be used to implement the above-described embodiments. A processor device may be a single processor, a plurality of processors, or combinations thereof. Processor devices may have one or more processor "cores."

Various embodiments of the present disclosure, as described above in the examples of FIGS. 1-5, may be implemented using computer system 600. After reading this description, it will become apparent to a person skilled in the relevant art how to implement embodiments of the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

As shown in FIG. 6, computer system 600 includes a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multiprocessor system, such system operating alone, or in a cluster of computing devices operating in a cluster or server farm. CPU 620 may be connected to a data communication infrastructure 610, for example, a bus, message queue, network, or multi-core message-passing scheme.

Computer system 600 also may include a main memory 640, for example, random access memory (RAM), and also may include a secondary memory 630. Secondary memory 630, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc. which is read by and written to by the removable storage drive. As will be appreciated by persons skilled in the relevant art, such a removable storage unit generally includes a computer usable storage medium having stored therein computer software and/or data.

In alternative implementations, secondary memory 630 may include other similar means for allowing computer programs or other instructions to be loaded into computer system 600. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to computer system 600.

Computer system 600 also may include a communications interface ("COM") 560. Communications interface 660 allows software and data to be transferred between computer system 600 and external devices. Communications interface 660 may include a modem, a network interface (such as an Ethernet card), a communications port, a PCM-CIA slot and card, or the like. Software and data transferred via communications interface 660 may be in the form of signals, which may be electronic, electromagnetic, optical, or other signals capable of being received by communications interface 660. These signals may be provided to communications interface 660 via a communications path of computer system 600, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Computer system 600 also may include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It would also be apparent to one of skill in the relevant art that the present disclosure, as described herein, can be implemented in many different embodiments of software, hardware, firmware, and/or the entities illustrated in the figures. Any actual software code with the specialized control of hardware to implement embodiments is not limiting of the detailed description. Thus, the operational behavior of embodiments will be described with the understanding that modifications and variations of the embodiments are possible, given the level of detail presented herein.

It is to be understood that both the foregoing general description and the following detailed description are exemplary and explanatory only and are not restrictive of the disclosed embodiments, as claimed.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for managing adherence of a user, having a blood glucose condition, to a prescribed regimen for treating the blood glucose condition, the method comprising:

receiving, using a processor, data related to the user, the data including information related to the prescribed regimen having one or more items or steps relating to each of medication, diagnostic testing, exercise, and diet, and a respective literacy level associated with each of the one or more items or steps, wherein the data related to the user includes blood glucose levels of the user measured by a blood glucose monitor and the medication includes insulin;

calculating the literacy level based on a survey completed by the user, based on an accuracy of data input by the user into an electronic device, wherein the data input by the user includes data relating to medication, diagnostic testing, exercise, and diet of the prescribed regimen, and based on whether the user did not enter certain data relating to one or more of medication, diagnostic testing, exercise, and diet of the prescribed regimen, wherein the literacy level is reduced when the user enters erroneous data or does not enter certain data relating to one or more of medication, diagnostic testing, exercise, and diet of the prescribed regimen;

calculating a compliance to quantity and a compliance to time for each of the one or more items or steps based on the received data, wherein compliance to time for each of the one or more items or steps relating to medication includes determining whether the user consumed a given medication within a window of time, wherein the value of the window of time is based on an expected timing of a future meal, and a dosage of the given medication to be consumed;

calculating an adherence count associated with each of the one or more items or steps by summing each of the compliance to quantity, the compliance to time, and the respective literacy level associated with each of the one or more items or steps;

determining a daily adherence for each of the one or more items or steps;

calculating a daily regimen adherence value by summing the daily adherence of all of the one or more items or steps in the regimen;

calculating a daily regimen baseline value by re-calculating the daily regimen adherence value by utilizing a maximum potential value for the adherence count for each of the respective items or steps in the regimen associated with the user;

determining an overall adherence value based on the daily regimen adherence value and the daily regimen baseline value;

comparing the overall adherence value with a threshold value;

generating a notification when the overall adherence value is less than the threshold value; and transmitting the generated notification to the electronic device, wherein the generated notification contains one or more intervention options including administration of a literacy survey and explanation to the user, via the electronic device, of benefits of following the prescribed regimen and impact of failure to follow the prescribed regimen.

2. The computer-implemented method of claim 1, wherein:

receiving data related to the user further comprises receiving a respective importance factor associated with each of the one or more items or steps; and determining a daily adherence for each of the one or more items or steps comprises determining the daily adherence for each of the one or more items or steps based on the adherence count and the importance factor associated with each of the one or more items or steps.

3. The computer-implemented method of claim 2, wherein determining the daily adherence for each of the one or more items or steps based on the adherence count and the importance factor associated with each of the one or more items or steps comprises multiplying the adherence count and the importance factor.

4. The computer-implemented method of claim 1, wherein calculating the compliance to quantity comprises:

determining a prescribed quantity for each of the one or more items or steps;

assigning quantity boolean values for actual quantity based on the prescribed quantity and the received data; and calculating the compliance to quantity based on the assigned quantity boolean values.

5. The computer-implemented method of claim 4, wherein calculating the compliance to time comprises:

determining a prescribed quantity time for each of the one or more items or steps;

assigning time boolean values for actual time based on the prescribed quantity time and the received data; and calculating the compliance to time based on the assigned time boolean values.

6. The computer-implemented method of claim 1, further comprising:

assigning a unique regimen identity to the regimen; and assigning respective unique identities to each of the one or more items or steps based on the unique regimen identity.

7. The computer-implemented method of claim 1, wherein the blood sugar condition is diabetes.

8. The computer-implemented method of claim 1, wherein at least some of the data is input by the user into the electronic device before being received using the processor.

9. A system for managing adherence of a user, the system comprising:

a memory having processor-readable instructions stored therein; and a processor configured to access the memory and execute the processor-readable instructions, which, when executed by the processor, configures the processor to perform a method, the method comprising:

receiving data related to the user, the data including information related to a prescribed regimen having one or more items or steps, and a respective literacy level associated with each of the one or more items or steps;

calculating the literacy level based on one or more of a survey completed by the user, an accuracy of data input by the user into an electronic device, wherein the data input by the user includes data relating to one or more of medication, diagnostic testing, exercise, and diet of the prescribed regimen, and based on whether the user did not enter certain data relating to one or more of medication, diagnostic testing, exercise, and diet of the prescribed regimen, wherein the literacy level is reduced when the user enters erroneous data or does not enter certain data relating to one or more of medication, diagnostic testing, exercise, and diet of the prescribed regimen;

calculating a compliance to quantity and a compliance to time for each of the one or more items or steps based on the received data;

calculating an adherence count associated with each of the one or more items or steps by summing at least two of the compliance to quantity, the compliance to time, and the respective literacy level associated with each of the one or more items or steps;

determining a daily adherence for each of the one or more items or steps;

calculating a daily regimen adherence value by summing the daily adherence of all of the one or more items or steps in the regimen;

calculating a daily regimen baseline value by re-calculating the daily regimen adherence value by utilizing a maximum potential value for the adherence count for each of the respective items or steps in the regimen associated with the user;

determining an overall adherence value based on the daily regimen adherence value and the daily regimen baseline value; and comparing the overall adherence value with a threshold value.

10. The system of claim 9, wherein the method further comprises:

generating a notification when the overall adherence value is less than the threshold value; and transmitting the generated notification to the electronic device, wherein the generated notification contains one or more intervention options.

11. The system of claim 10, wherein:

receiving data related to the user further comprises receiving a respective importance factor associated with each of the one or more items or steps; and determining a daily adherence for each of the one or more items or steps comprises multiplying the adherence count and the importance factor.

12. The system of claim 9, wherein calculating the compliance to quantity comprises:

determining a prescribed quantity for each of the one or more items or steps;

assigning quantity boolean values for actual quantity based on the prescribed quantity and the received data; and calculating the compliance to quantity based on the assigned quantity boolean values.

13. The system of claim 12, wherein calculating the compliance to time comprises:
   determining a prescribed quantity time for each of the one or more items or steps;
   assigning time boolean values for actual time based on the prescribed quantity time and the received data; and
   calculating the compliance to time based on the assigned time boolean values.

14. The system of claim 9, wherein the method further comprises:
   assigning a unique regimen identity to the regimen; and
   assigning respective unique identities to each of the one or more items or steps based on the unique regimen identity.

15. A non-transitory computer-readable medium storing instructions, the instructions, when executed by a computer system, cause the computer system to perform a method, the method comprising:
   receiving, using a processor, data related to a user, the data including information related to a prescribed regimen having one or more items or steps relating to one or more of medication, diagnostic testing, exercise, and diet, a respective literacy level associated with each of the one or more steps;
   calculating the literacy level based on a survey completed by the user, based on an accuracy of data input by the user into an electronic device, wherein the data input by the user includes data relating to medication, diagnostic testing, exercise, and diet of the prescribed regimen, and based on whether the user did not enter certain data relating to one or more of medication, diagnostic testing, exercise, and diet of the prescribed regimen, wherein the literacy level is reduced when the user enters erroneous data or does not enter certain data relating to one or more of medication, diagnostic testing, exercise, and diet of the prescribed regimen;
   calculating a compliance to quantity and a compliance to time for each of the one or more items or steps based on the received data, wherein calculating compliance to quantity includes determining a prescribed quantity for each of the one or more items or steps, assigning quantity boolean values for actual quantity based on the prescribed quantity and the received data, and calculating the compliance to quantity based on the assigned quantity boolean values, and wherein calculating compliance to time includes determining a prescribed quantity time for each of the one or more items or steps, assigning time boolean values for actual time based on the prescribed quantity time and the received data, and calculating the compliance to time based on the assigned time boolean values;
   calculating an adherence count associated with each of the one or more items or steps by summing the compliance to quantity, the compliance to time, and the respective literacy level for each of the one or more items or steps based on the received data;
   determining a daily adherence for each of the one or more items or steps;
   calculating a daily regimen adherence value by summing the daily adherence of all of the one or more items or steps in the regimen;
   calculating a daily regimen baseline value by re-calculating the daily regimen adherence value by utilizing a maximum potential value for the adherence count for each of the respective items or steps in the regimen associated with the user;
   determining an overall adherence value based on the daily regimen adherence value and the daily regimen baseline value;
   comparing the overall adherence value with a threshold value;
   generating a notification when the overall adherence value is less than the threshold value; and
   transmitting the generated notification to the electronic device, wherein the generated notification contains one or more intervention options.

16. The non-transitory computer-readable medium of claim 15, wherein:
   receiving data related to the user further comprises receiving a respective importance factor associated with each of the one or more items or steps; and
   determining a daily adherence for each of the one or more items or steps comprises multiplying the adherence count and the importance factor.

17. The system of claim 9, wherein compliance to time for each of the one or more items or steps relating to medication includes determining whether the user consumed a given medication within a window of time, wherein the value of the window of time is based on an expected timing of a future meal, and a dosage of the given medication to be consumed.

18. The system of claim 10, wherein the generated notification contains one or more intervention options including administration of a literacy survey and explanation to the user, via the electronic device, of benefits of following the prescribed regimen and impact of failure to follow the prescribed regimen.

19. The non-transitory computer readable medium of claim 15, wherein compliance to time for each of the one or more items or steps relating to medication includes determining whether the user consumed a given medication within a window of time, wherein the value of the window of time is based on an expected timing of a future meal, and a dosage of the given medication to be consumed.

20. The non-transitory computer readable medium of claim 19, wherein compliance to time for each of the one or more items or steps relating to medication includes determining whether the user consumed a given medication within a window of time, wherein the value of the window of time is based on an expected timing of a future meal, and a dosage of the given medication to be consumed.

* * * * *